(12) United States Patent
Doan et al.

(10) Patent No.: US 7,145,024 B2
(45) Date of Patent: Dec. 5, 2006

(54) PROCESS FOR PREPARING PROTEASE INHIBITOR INTERMEDIATES

(75) Inventors: Brian Daniel Doan, King of Prussia, PA (US); Roman D Davis, Durham, NC (US); Thomas Claiborne Lovelace, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 261 days.

(21) Appl. No.: 10/490,186

(22) PCT Filed: Sep. 16, 2002

(86) PCT No.: PCT/US02/29315

§ 371 (c)(1),
(2), (4) Date: Mar. 19, 2004

(87) PCT Pub. No.: WO03/024974

PCT Pub. Date: Mar. 27, 2003

(65) Prior Publication Data

US 2004/0204595 A1    Oct. 14, 2004

Related U.S. Application Data

(60) Provisional application No. 60/323,692, filed on Sep. 20, 2001.

(51) Int. Cl.
*C07D 493/06* (2006.01)
(52) U.S. Cl. .................................. 549/464
(58) Field of Classification Search .............. 549/464
See application file for complete search history.

(56) References Cited

FOREIGN PATENT DOCUMENTS

WO        96/26749        11/1994

OTHER PUBLICATIONS

Schrieber, Stuart L., et al., "The furan-carbonyl photocycloaddition reaction: determination of the absolute stereostructure of asteltoxin," *Tetrahedron Letters*, 1986, vol. 27, No. 23, pp. 2575-2578.
Schrieber, Stuart L., et al., "Use of unsymmetrically substituted furans in the furan-carbonyl photocycloaddition reaction. Synthesis of a kadsurenone-ginkgolide hybrid," *Tetrahedron Letters*, 1988, vol. 29, No. 51, pp. 6689-6692.

Ghosh, A.K. et al., "Nonpeptidal P2 Ligands for HIV protease Inhibitors: Structure-Based Design Synthesis and Biological Evaluation," *Journal of Medicinal Chemistry*, 1996, vol. 39, pp. 3278-3290.
Hambalek, R., et al. "A Short Synthesis of (+ )-Oxetanocin." Tetrahedron Letters, vol. 31, No. 38, pp. 5445-5448, 1990.
Hambalek, R., et al. "Trisubstituted Oxetanes from 2, 7-Dioxa-Bicyclo-[3,2,0]-Hept-3-ENES." Tetrahedron Letters, vol. 31, No. 33, pp. 4693-4696, 1990.
Hattori, K., et al. "The Undesirable Lability of tert-butyldimethylsilyl Ethers Unders Pd/C-catalyzed Hydrogenation Conditions and Solution of the Problem by Using a Pd/C(en) Catalyst." Tetrahedron Letters, vol. 41, pp. 5711-5714, 2000.
Kozluk, T., et al. " The Synthesis of 3-Deoxy-DL-Streptose." Tetrahedron, vol. 39, No. 5, pp. 805-810, 1983.
Powell, N.A., et al. "Anti-1,3-diols by Addition of Dialkylzinc Reagents to 4-Acctoxy-1,3-dioxanes." J. Org. Chem., vol. 64, pp. 2026-2037, 1999.
Schreiber, S.L., et al. "A Photochemical Route to the formation of Threo." J. Am. Chem. Soc., vol. 105, pp. 600-661, 1983.
Schreiber, S.L., et al. "Application of the Furan-Carbonyl Photocycloaddition Reaction to the Synthesis of the Bis(tetrahydrofuran) Moiety of Asteltoxin." J. Am. Chem. Soc., vol. 105, pp. 6723-6724, 1983.
Schreiber, S.L., et al. "Synthetic Studies of the furan-Carbonyl Photocycloaddition Reaction. A Total Synthesis of (+ )-Avenaciolide." J. Am. Chem.. Soc., vol. 106, No. 23, pp. 7200-7202, 1984.
Schreiber, S.L., et al. "Total Synthesis of (+)-Asteltoxin." J. Am. Chem.. Soc., vol. 106, pp. 4186-4888, 1984.
Shima, K., et al. "Organic Photochemical Reactions. IV. Photoaddition Reactions of Various Carbonyl Compounds to Furan." Bull. Chem.. Soc. Japan, vol. 39, No. 8, pp. 1806-1808, 1966.
Toki, S., et al. "Organic Photochemical Reactions I. The Synthesis of Substituted Oxetanes by the Photoaddition of Aldehydes to Furans." Photochemical Synthesis of Oxetanes, vol. 38, No. 5, pp. 760-762, May 1965.
Zamojski, A., et al. "Synthesis of 3-Substituted Furans." J. Org. Chem., vol. 42, No. 6, pp. 1089-1090, 1977.
PCT Written Opinion.

*Primary Examiner*—Taofiq Solola
(74) *Attorney, Agent, or Firm*—Amy H. Fix

(57) ABSTRACT

The present invention includes a method for preparing cyclic alcohols. The method includes a reduction, deprotection, and rearrangement scheme. The present invention further provides a method of preparation of an intermediate useful in the synthesis of compounds that function as inhibitors of the aspartyl protease enzyme of human immunodeficiency virus (HIV).

15 Claims, No Drawings

PROCESS FOR PREPARING PROTEASE INHIBITOR INTERMEDIATES

This application is filed pursuant to 35 U.S.C. § 371 as a United States National Phase Application of International Application No. PCT/US02/29315 filed Sep. 16, 2002, which claims priority from US 60/323,692 filed Sep. 20, 2001.

FIELD OF THE INVENTION

The present invention generally concerns the preparation of cyclic alcohol intermediates useful in the preparation of inhibitors of HIV aspartyl protease. More specifically, the present invention includes a method for the preparation of (3α,3aβ,6aβ)-hexahydrofuro[2,3-b]furan-3-ol.

BACKGROUND OF THE INVENTION

The human immunodeficiency virus ("HIV") is the causal agent for acquired immunodeficiency syndrome ("AIDS"), and its precursor AIDS-related complex ("ARC"). AIDS is a: disease characterized by the destruction of the immune system, particularly the destruction of $CD4^+$ T-cells, with attendant susceptibility to opportunistic infections. ARC is a syndrome characterized by symptoms such as persistent generalized lymphadenopathy, fever, and weight loss.

Among the drugs currently used to treat HIV infections in humans are those that inhibit the HIV aspartyl protease enzyme. Drugs that are used as protease inhibitors are, in general, chemically complex and are difficult to prepare in a cost-effective and efficient manner.

For example, WO 94/26749 discloses the preparation of the intermediate hexahydrofuro[2,3-b]furan-3-ol, as well as its use in the preparation of compounds that are effective inhibitors of HIV aspartyl protease. This method disclosed for the preparation of the hexahydrofuro[2,3-b]furan-3-ol subunit is a multi-step procedure that relies on a citrate derivative as starting material. This method requires the initial preparation of an enantiomerically pure starting material, followed by six additional chemical steps. A more efficient method would be preferable for savings in time, materials, and other valuable resources.

Another synthesis of the intermediate hexahydrofuro[2,3-b]furan-3-ol subunit was described by Ghosh, et. al. in *Nonpeptidal P₂ Ligands for HIV Protease Inhibitors: Structure-Based Design, Synthesis and Biological Evaluation*, J. Med. Chem., 39(17), p.3278, 1996. A key step in this preparation of the hexahydrofuro[2,3-b]furan ring system is the cyclization of a 2-(2-propynyloxy)tetrahydrofuranyl derivative under radical cyclization conditions. For example, 3-iodo-2-(2-propynyloxy)tetrahydrofuran could be cyclized to the desired 3-methylene hexahydrofuro[2,3-b]furan derivative using stoichiometric amounts of compounds capable of acting as radical initiators, such as a mixture of sodium borohydride and cobaloxime. Alternatively, the same cyclization reaction can be effected using a stoichiometric amount of a trialkyltin hydride, such as tributyltin hydride. There are disadvantages, however, to such methods for the synthesis of pharmaceutical intermediates. For example, the toxicity of trace amounts of metals such as cobalt or tin poses a potential disadvantage of such methods.

Based upon the disadvantages of the present methods for the formation of protease inhibitor intermediates, new and more efficient methods for their preparation are of value. Preferably, any new method would use readily available, achiral starting materials. Additionally, the method preferably consists of fewer chemical steps than previously published methods and, therefore, be more amenable to scale-up synthesis.

SUMMARY OF THE INVENTION

As shown in the following Summary Scheme, the present invention includes a method for preparing cyclic alcohols, preferably (3α,3aβ,6aβ)-hexahydrofuro[2,3-b]furan-3-ol. The present method includes preparation of an oxetane intermediate by means of a photochemical cycloaddition reaction. The method also includes a reduction, deprotection, and rearrangement scheme.

The present invention includes a method for the preparation of a cyclic alcohol of formula (IV)

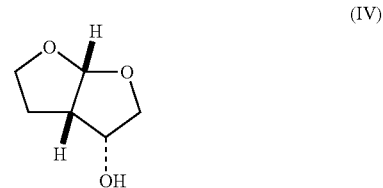

(IV)

comprising reducing, deprotecting, and rearranging, in non-aqueous telescoping conditions, an oxetane of formula (II)

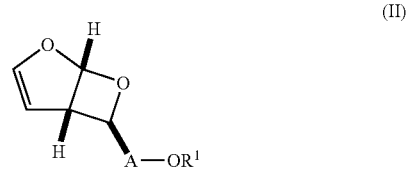

(II)

wherein A is —$CH_2$— and
$R^1$ is
—$C(R^2)_3$, where each $R^2$ is independently selected from the group consisting of H, alkyl, and aryl;
—$C(O)R^3$, wherein $R^3$ is selected from the group consisting of alkyl and aryl; or
—$Si(R^3)_3$, wherein each $R^3$ is independently as defined above. As used herein the phrase "non-aqueous" refers to avoiding the use of water as a reagent, but includes the use of water as a solvent or in a work-up, as will be appreciated by those skilled in the art.

In one preferred embodiment, $R^1$ is —$C(R^2)_3$, one $R^2$ is —$CH_3$, one $R^2$ is —$CH_3$, and one $R^2$ is phenyl and the reduction, deprotection, and rearrangement is conducted in situ with palladium on carbon with one of formic acid, ammonium formate, or hydrogen. More preferably the in situ reaction agent is palladium on carbon with hydrogen. More preferably the catalyst is 10% Pd/C. Preferably the reduction, deprotection, and rearrangement is conducted in situ with a solvent selected from the group consisting of methanol, ethanol, ethyl acetate, dimethoxyethane, and THF. More preferably the solvent is THF.

In another preferred embodiment, $R^1$ is —$Si(R^3)_3$, wherein each $R^3$ is $C_{1-8}$ alkyl.

Another aspect of the present invention includes further resolving the cyclic alcohol to provide an enantioenriched mixture, more preferably resolving the cyclic alcohol to provide an enantiomerically pure cyclic alcohol.

Another aspect of the present invention includes a method for the preparation of hexahydrofuro[2,3-b]furan-3-ol, comprising:

a) reacting a compound of formula (I) with furan in the presence of light;

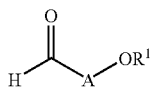

wherein A is —CH$_2$— or —C(O)—, provided that when A is —CH$_2$—

R$^1$ is selected from:
—C(R$^2$)$_3$, where each R$^2$ is independently selected from the group consisting of H, alkyl, and aryl;
—C(O)R$^3$, wherein R$^3$ is selected from the group consisting of alkyl and aryl; or
—Si(R$^3$)$_3$, wherein each R$^3$ is independently as defined above; and when A is —C(O)—, R$^1$ is selected from alkyl or aryl;

to produce a 2,7-dioxabicyclo[3.2.0]hept-3-ene derivative; and reducing, deprotecting, and rearranging in non-aqueous telescoping conditions the 2,7-dioxabicyclo[3.2.0]hept-3-ene derivative to produce hexahydrofuro[2,3-b]furan-3-ol.

Thereafter, preferably the method further includes resolving the hexahydrofuro[2,3-b]furan-3-ol. More preferably the resolution includes
i) reacting (3α,3aβ,6aβ)-hexahydrofuro[2,3-b]furan-3-ol with an acylating agent to afford an acyl derivative; and
ii) reacting said acyl derivative with an esterase enzyme to afford (3R,3aS,6aR)-hexahydrofuro[2,3-b]furan-3-ol.

In one embodiment R$^1$ is —Si(R$^3$)$_3$, whereby the method further includes cleaving the silyl group.

In another embodiment R$^1$ is —C(O)R$^3$—, whereby the method further includes a hydride reduction. Preferably the hydride reduction includes using an agent selected from the group consisting of aluminum hydride, di-isobutylaluminum hydride, lithium aluminum hydride, borane, and modified sodium borohydride.

One preferred embodiment includes reaction of 2,7-dioxabicyclo[3.2.0]hept-6-ylmethanol to afford an alcohol that is an intermediate useful for the preparation of protease inhibitors, such as the intermediate hexahydrofuro[2,3-b]furan-3-ol.

The present invention further provides a method of preparation of an intermediate useful in the synthesis of compounds that function as inhibitors of the aspartyl protease enzyme of human immunodeficiency virus (HIV). The hexahydrofuro[2,3-b]furan-3-ol derived from the present invention may be resolved to afford (3R,3aS,6aR)-hexahydrofuro[2,3-b]furan-3-ol, an intermediate particularly useful in the synthesis of compounds effective as inhibitors of HIV aspartyl protease.

DETAILED DESCRIPTION OF THE PREFERRED EMBODIMENT

Throughout this specification, the term "alkyl", alone or in combination with any other term, refers to a linear-chain or branched-chain saturated aliphatic hydrocarbon radical, preferably containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl, and the like.

The term "aryl," alone or in combination with any other term, refers to a carbocyclic aromatic radical, preferably containing the specified number of carbon atoms. Examples of aryl radicals include, but are not limited to phenyl, benzyl, naphthyl, indenyl, indanyl, azulenyl, fluorenyl, anthracenyl, and the like. The term "aryl" as used herein includes alkylaryls, such as benzyl. In addition, the aryl ring may be optionally substituted with one or more groups independently selected from the group consisting of halogen, C$_{1-8}$ alkyl, —CF$_3$, heterocycle, —OCH$_3$, aryl, C$_{1-8}$ alkylaryl, and C$_{1-8}$ alkylheterocycle.

The term "halogen" refers to a radical of chlorine, bromine, or iodine.

The term "aldehyde" as used generally herein refers to a compound of formula (I):

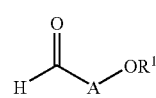

formula I where A may be —CH$_2$— or —C(O)— and R$^1$ is as defined below. Thus, as used herein, the term encompasses both acetaldehydes and glyoxylates. As used herein, therefore, the term aldehyde includes, for example, tert-butyldimethylsilyloxy acetaldehyde, (1-methyl-1phenylethoxy)acetaldehyde, tert-butoxyacetaldehyde, benzyloxyacetaldehyde, and ethyl glyoxylate.

The term "catalyst" or "hydrogenation catalyst" inlcudes any suitable catalyst for performing the reductions described herein. Non-limiting examples of catalysts include the transition-metal catalysts, such as platinum, palladium, iridium, rhodium, ruthenium, and the like.

The term "cyclic" includes mono- and multi-cyclic ring systems, further including fused and bridged multi-cyclic ring systems.

The terms "racemic mixture" and "racemate" refer to a mixture of enantiomers.

The term "enantiomer" refers to a compound that contains at least one stereochemical center and is of either the "R" or "S" configuration. The enantiomer may be in a mixture with the enantiomer of opposite stereoconfiguration, i.e. the antipode. If the two enantiomers are in a mixture in equal proportions, the mixture is termed a "racemic mixture." Alternatively, if the two enantiomers exist in a mixture in which one enantiomer is present in amounts greater (more than 50%) than the opposite enantiomer, the mixture is termed "enantioenriched." If the two enantiomers are present in admixture in which one enantiomer comprises 95% or more of the mixture, the mixture is termed "enantiomerically pure."

The term "flow-cell reactor" refers to a vessel that is suitable for use in chemical reactions. In general, a vessel suitable for use as a flow-cell reactor for photolytic chemical reactions comprises a hollow container with a smooth, reflective interior, constructed of a suitable material, preferably stainless steel, an inlet and outlet suitable for the introduction and removal of a chemical reaction mixture, and a light source capable of providing light to the reaction mixture. Preferably, the light has a wavelength of about 290–320 nanometers, preferably about 300–320 nanometers, more preferably from about 300–315 nanometers, and most preferably from about 300–310 nanometers.

One preferred aspect of the present invention concerns a method for the preparation of (3α,3aβ,6aβ)-hexahydrofuro[2,3-b]furan-3-ol. The present invention further preferably includes its subsequent resolution to afford (3R,3aS,6aR)-hexahydrofuro[2,3-b]furan-3-ol, an intermediate useful in the synthesis of inhibitors of HIV aspartyl protease.

The present invention is summarized in Schemes 1–3 below:

Scheme 1

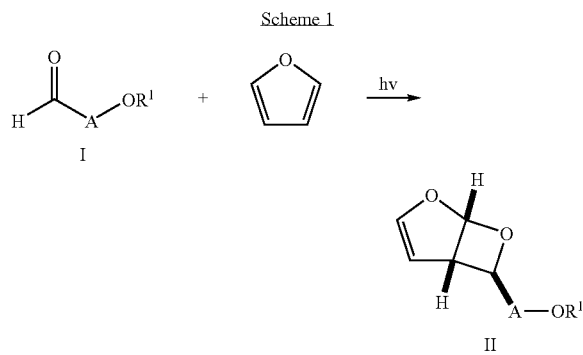

Scheme 2

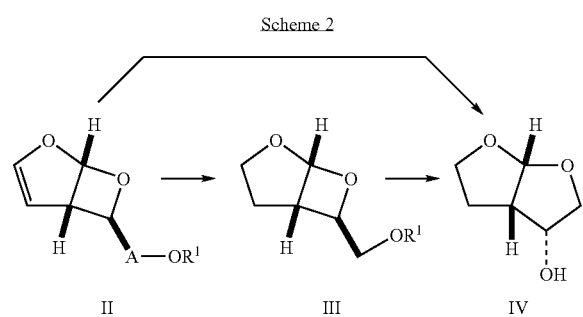

Scheme 3

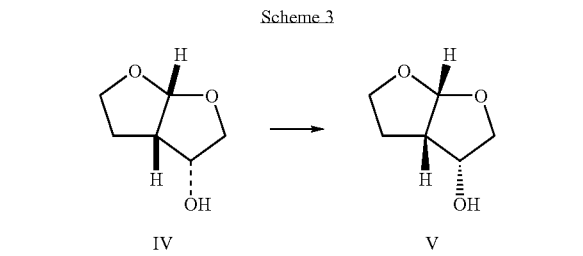

wherein for each occurrence A may be —CH$_2$— or —C(O)—, provided that when A is —CH$_2$—, R$^1$ is selected from:
- —C(R$^2$)$_3$, where each R$^2$ is independently selected from the group consisting of H, C$_{1-8}$ alkyl, and C$_{6-14}$ aryl;
- —C(O)R$^3$, wherein R$^3$ is selected from the group consisting of C$_{1-8}$ alkyl and C$_{6-14}$ aryl; or
- —Si(R$^3$)$_3$, wherein each R$^3$ is independently selected and as defined above; and when A is —C(O)—, R$^1$ is selected from C$_{1-8}$ alkyl or C$_{6-14}$ aryl.

In one embodiment, when A is —CH$_2$—, preferably R$^1$ is —C(R$^2$)$_3$, wherein each R$^2$ is CH$_3$. Alternatively, when A is —CH$_2$—, preferably R$^1$ is —C(R$^2$)$_3$, wherein one R$^2$ is CH$_3$, the second R$^2$ is CH$_3$, and the third R$^2$ is aryl. Alternatively, when A is —CH$_2$—, preferably R$^1$ is —Si(R$^3$)$_3$, wherein one R$^3$ is tert-butyl, and the second and third R$^3$ are each CH$_3$.

Particularly preferred compounds of formula (I) include tert-butyldimethyl silyloxyacetaldehyde, (1-methyl-1phenylethoxy)acetaldehyde, tert-butoxyacetaldehyde, and benzyloxyacetaldehyde.

While the schemes herein represent the preferred relative stereochemistry, the present invention should not be limited to a particular absolute stereochemistry. As illustrated herein, structures may be depicted using heavy and dashed lines. In such case, the heavy and dashed lines represent preferred enantiomeric mixtures with relative stereochemistry as depicted. For example, the compound of formula IV illustrates an enantiomeric mixture of (3α,3aβ,6aβ)-hexahydrofuro[2,3-b]furan-3-ol. Nevertheless, racemic mixtures and enantioenriched mixtures of the antipode are included within the scope of the present invention.

As illustrated herein, heavy and dashed wedges represent a preferred single enantiomer with the stereochemistry depicted, such as, for example, the compound of formula V is meant to represent (3R,3aS,6aR)-hexahydrofuro[2,3-b]furan-3-ol. As shown above, the compound of formula (V), in which the bonds to the chiral centers are drawn using "wedges," represents either enantiomerically pure (3R,3aS,6aR)-hexahydrofuro[2,3-b]furan-3-ol or an enantioenriched mixture.

As shown in the above-referenced schemes, the present invention includes a photoaddition reaction of a protected aldehyde (formula (I)) to afford an oxetane (formula (II)). The oxetane is subsequently reduced to afford formula (III). Then, the invention includes deprotection and rearrangement to afford a cyclic alcohol (formula (IV)). An alternate embodiment of the present invention includes treatment of the oxetane (formula (II)) to a reduction/deprotection/rearrangement reaction to afford a cyclic alcohol (formula (IV)).

More specifically, as illustrated by Scheme 1, a first embodiment includes a aldehyde (formula (I)) that is allowed to react with furan in the presence of light to afford a compound of formula (II), namely, an oxetane. While particular protecting groups are defined above (with reference to R$^1$), the scope of the present invention should extend to any appropriate protecting group. Preferred protecting groups include t-butyl, cumyl, and substituted silyl groups.

Preferably, the light has a wavelength of about 290–320 nanometers, more preferably about 300–320 nanometers, more preferably from about 300–315 nanometers, and most preferably from about 300–310 nanometers. The reaction preferably is performed in a solvent, such as tetrahydrofuran, toluene, or furan, with furan being preferable. The reaction preferably is performed at a temperature of about 0° C. to 20° C., preferably about 10° C. The reaction preferably is performed in a reaction vessel capable of acting as a flow-cell reactor.

Compounds of formula (I) are commercially available or can be prepared by methods known in the art. For example, see M. J. Shiao, et. al. *Synthetic Communications* 1988, Vol. 18, No. 4, pp. 359–366; C. K. F. Shen, et. al. *J. Org. Chem.* 1996, Vol. 61, pp. 9242–9244; T. M. Yuan, et. al. *Synlett* 1996, pp. 53–54; and W. L. Cheng, et. al. *J. Org. Chem.* 1999, Vol. 64, pp. 532–539; M. J. Brown, L. E. Overman *J.*

Org. Chem. 1991, Vol. 56, pp. 1933, each herein incorporated by reference as related to the preparation of hydroxyacetaldehydes.

As illustrated by Scheme 2 above, the present invention includes a process for the preparation of a compound of formula (III) through reduction of the olefinic bond of the oxetane of formula (II). Such a reduction, as stated above, may be conducted with a hydrogenation catalyst, such as either platinum on carbon or palladium on carbon, in conjunction with hydrogen and base. One preferable reduction involves a combination of agents including platinum on carbon in combination with hydrogen. These reactions may be conducted in any appropriate solvent. Examples of preferred solvents include ethyl acetate, methanol, ethanol, and more preferably, tetrahydrofuran. In addition, the use of an agent capable of acting as a base is preferred in order to prevent the formation of unwanted products. Although any agent capable of acting as a base may be used, in other words any ionic or molecular species capable of accepting or receiving a proton from another substance, preferred agents include sodium carbonate and potassium carbonate, more preferably potassium carbonate.

As noted above, the invention includes a process for the preparation of a compound of formula (III) through reduction of the olefinic bond of the oxetane of formula (II). As will be appreciated by those skilled in the art, several of the compounds included within the present invention are esters. In the event A is —C(O)— or in the event $R^1$ is —C(O)$R^3$—, such compounds may be reduced prior to the reduction of the olefinic bond of the oxetane. Thus, such reduction of the esters will result in a compound of formula (II) where A is $CH_2$ and $R^1$ is H.

For example, when A is —C(O)—, the present invention may include a hydride reduction, such as reaction with a base such as aluminum hydride, di-isobutylaluminum hydride, lithium aluminum hydride, borane, or modified sodium borohydride. See, e.g., S Daluge; M. Martin; B Sickles; D. Livingston *Nucleosides, Nucleotide &Nucleic Acids* 19 (1&2), 297–327 (2000), herein incorporated by reference as related to such reactions. These reactions may be performed in a solvent such as diethyl ether or, preferably, tetrahydrofuran. Preferably, these reactions may be performed at a temperature from about –78° C. to 50° C., more preferably about 0° C. to 10° C.

Similarly, such a hydride reduction may be used when $R^1$ is —C(O)$R^3$—. Alternatively, a base hydrolysis step may be used. Although any base may be used for the base hydrolysis, preferred bases include sodium hydroxide, lithium hydroxide, potassium hydroxide, potassium carbonate, sodium methoxide, ammonium hydroxide, sodium ethoxide, with solvents such as methanol, ethanol, or mixtures of methanol and water, ethanol and water, or tetrahydrofuran and water.

Thereafter the olefinic bond of the oxetane is reduced to afford compounds of formula (III).

The compound of formula (III) is then deprotected and rearranged to afford a compound of formula (IV). The deprotection and rearrangement reaction is performed with either (i) a catalyst, such as a palladium reagent, with hydrogen; or (ii) with an agent capable of acting as a Lewis acid; or (iii) with an agent capable of acting as a Brönsted acid. As used herein, the terms Lewis acid and Brösted acid have their meanings as accepted in the art. Namely, "Lewis acid" refers to a substance that can accept an electron pair from a base and "Brönsted acid" refers to a species that can act as a source of protons.

Although any appropriate palladium reagent may be used to effect this reaction, preferably palladium on carbon, and more preferably 10% by weight palladium on carbon is used. Reactions that use a palladium reagent to affect the conversion of a compound of formula (III) to a compound of formula (IV) should be conducted in the presence of an additional compound capable of acting as a reductant, such as hydrogen. Additionally, the reactions may be conducted in a solvent such as methanol, ethanol, or tetrahydrofuran. More preferably tetrahydrofuran is used.

Similarly, although any agent capable of acting as a Lewis acid may be used, preferred agents are selected from boron trifluoride etherate, iron (II) chloride on silica, tin (IV) chloride, or aluminum (III) chloride. Reactions that use a Lewis acid to affect the conversion of a compound of formula (III) to a compound of formula (IV) may be conducted in an aprotic solvent. Examples of preferred aprotic solvents include tetrahydrofuran, dichloromethane, or chloroform.

Likewise, although any agent capable of acting as a Brönsted acid may be used preferred agents include acetic acid, sulfuric acid, nitric acid, hydrobromic acid, or, most preferably, hydrochloric acid. Reactions that use a Brönsted acid to affect the conversion of a compound of formula (III) to a compound of formula (IV) may be conducted in a solvent such as methanol, ethanol, or tetrahydrofuran. More preferably, tetrahydrofuran is used.

When $R^1$ is —Si($R^3$)$_4$, any appropriate agent capable of cleaving the silyl protecting group may be used, preferably a fluoride ion source. Particularly preferred compounds are of formula $^+N(R^3)_4X^-$, wherein each $R^3$, which may be the same or different, are selected from the group consisting of $C_{1-8}$alkyl and $C_{6-14}$aryl, and X is halogen, preferably fluorine. These agents are commercially available or can be prepared by methods known in the art. These cleaving reactions are typically performed in a solvent such as methanol, ethanol, tetrahydrofuran, chloroform, or, more preferably, dichloromethane. The cleaving reactions are performed at a temperature from about 0° C. to 50° C., and more preferably at about ambient temperatures.

The following represent examples of some embodiments of the present invention:

EXAMPLE I

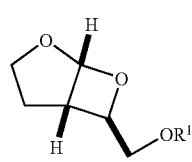

formula III wherein $R^1$ is —C(CH$_3$)$_3$, is reacted with an agent capable of acting as a Lewis acid or a Brönsted acid to afford a compound of formula (IV).

Preferred Lewis acids include boron trifluoride etherate, iron (III) chloride on silica, tin (IV) chloride, zinc (II) bromide, or aluminum (III) chloride and preferred solvents are tetrahydrofuran, dichloromethane, or chloroform.

Preferred Brönsted acids include trifluoroacetic acid, sulfuric acid, nitric acid, hydrobromic acid, or, most preferably, hydrochloric acid. Preferred solvents include methanol, ethanol, tetrahydrofuran, water, a mixture of tetrahydrofuran and water, or, most preferably, 2,2,2-trifluoroethanol.

EXAMPLE II

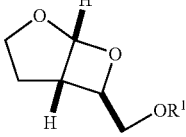

formula III wherein $R^1$ is —$Si(R^3)_4$, wherein $R^3$ is $C_{1-8}$ alkyl, is reacted with an agent capable of cleaving the silyl protecting group to afford a compound of formula (II), wherein $R^1$ is hydrogen. Although any appropriate agent capable of cleaving the silyl-protecting group may be used, preferably the cleavage is performed with hydrochloric acid in tetrahydrofuran and water to afford the alcohol of formula (IV).

Additionally, compounds of formula $^+N(R^3)_4X^-$, wherein each $R^3$, which may be the same or different, are selected from the group consisting of $C_{1-8}$alkyl and $C_{6-14}$-aryl, and X is fluorine may be used. These agents are commercially available or can be prepared by methods known in the art. The cleaving reactions are typically performed in a solvent such as methanol, ethanol, tetrahydrofuran, tetrahydrofuran and water, chloroform, or, dichloromethane. The cleaving reactions are performed at a temperature from about 0° C. to 50° C., and more preferably at about ambient temperatures. Thereafter, a compound of formula (III), wherein $R^1$ is hydrogen is reacted with either (i) a palladium reagent with hydrogen, or with (ii) an agent capable of acting as a Lewis acid, or with (iii) an agent capable of acting as a Brösted acid.

As noted above, a preferred palladium reagent is 10% by weight palladium on carbon, in the presence of an additional compound capable of acting as a reductant, preferably hydrogen. Additionally, the palladium reactions preferably are conducted in a mixture of tetrahydrofuran and water.

For this embodiment, preferred Lewis acids include boron trifluoride etherate, iron (III) chloride on silica, tin (IV) chloride, or aluminum (III) chloride and preferred solvents include tetrahydrofuran, dichloromethane or chloroform.

For this embodiment, preferred Brösted acids include acetic acid, sulfuric acid, nitric acid, hydrobromic acid, or more preferably hydrochloric acid and preferred solvents are methanol, ethanol, tetrahydrofuran, water, or, more preferably, a mixture of tetrahydrofuran and water.

EXAMPLE III

As noted above, an alternate embodiment of the present invention includes treatment of the oxetane (formula (II)) to a reduction/deprotection/rearrangement reaction to afford directly a cyclic alcohol (formula (IV)). Thus,

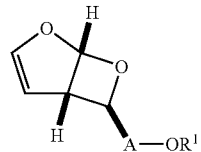

formula II wherein A is —$CH_2$— and $R^1$ is —$C(R^2)_3$, where two $R^2$ are H, or two $R^2$ are $CH_3$, and one $R^2$ is $C_{6-14}$ aryl, is reacted with 5% by weight palladium on carbon in combination with formic acid, ammonium formate, or preferably hydrogen. More preferably, 10% by weight palladium on carbon is used in combination with hydrogen. These reactions preferably are conducted in a solvent such as methyl alcohol, ethyl alcohol, or, more preferably, tetrahydrofuran. In addition, these reactions preferably are conducted at a temperature from about 10° C. to 50° C., more preferably at about ambient temperature.

EXAMPLE IV

As noted above, certain substituents on the oxetane intermediate should be treated prior to the reduction, deprotection, and rearrangement reactions of the present invention. Thus, for example,

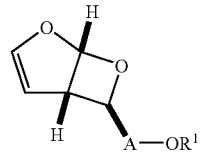

formula II wherein A is —C(O)— and $R^1$ is independently selected from $C_{1-8}$alkyl or $C_{6-10}$aryl, is reacted preferably with a base such as aluminum hydride, di-isobutylaluminum hydride, lithium aluminum hydride, borane, or modified sodium borohydride. See, e.g., S Daluge; M. Martin; B Sickles; D. Livingston *Nucleosides, Nucleotide &Nucleic Acids* 19 (1&2), 297–327 (2000), herein incorporated by reference as related to such reactions. These reactions may be performed in a solvent such as diethyl ether or, preferably, tetrahydrofuran. Preferably, these reactions may be performed at a temperature from about −78° C. to 50° C., more preferably about 0° C. to 10° C.

Thereafter, a compound of formula (III) is reacted with either (i) a palladium reagent, or with (ii) an agent capable of acting as a Lewis acid, or with (iii) an agent capable of acting as a Brösted acid.

EXAMPLE V

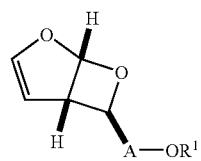

formula II wherein A is —CH$_2$— and R$^3$ is —C(O)R$^3$, wherein R$^1$ is selected from the group consisting of C$_{1-8}$alkyl or C$_{6-14}$aryl, is reacted with a base, such as aluminum hydride, modified sodium borohydride (see, S Daluge; M. Martin; B Sickles; D. Livingston *Nucleosides, Nucleotide &Nucleic Acids* 19 (1&2), 297–327 (2000)) or lithium aluminum hydride. These reactions may be performed in a solvent such as diethyl ether or preferably tetrahydrofuran. In addition, these reactions may be performed at a temperature from −78° C. to 50° C., preferably 0° C. to 10° C.

Alternatively, hydrolysis of the ester to the alcohol through basic hydrolysis may be used, with preferred agents including bases such as sodium hydroxide, lithium hydroxide, potassium hydroxide, potassium carbonate, sodium methoxide, ammonium hydroxide, sodium ethoxide. Preferably, potassium carbonate is used in a protic solvent such as methanol, ethanol, or mixtures of methanol and water, ethanol and water, or tetrahydrofuran and water. Preferably methanol is the solvent. These reactions may be performed at about 0° C. to 60° C. but more preferably at about 25° C.

Thereafter, a compound of formula (I) is reacted with either (i) a palladium reagent, or with (ii) an agent capable of acting as a Lewis acid, or with (iii) an agent capable of acting as a Brösted acid.

Another aspect of the invention, as illustrated generally in Scheme 3, provides for the resolution of a racemic mixture of (3α,3aβ,6aβ)-hexahydrofuro[2,3-b]furan-3-ol (IVa) to provide an enantioenriched mixture of each enantiomer. While any appropriate method to resolve the mixture may be used, one preferred method includes conversion to a diastereomeric mixture followed by separation. More specifically, a racemic mixture of (3α,3aβ,6aβ)-hexahydrofuro[2,3-b]furan-3-ol, formula (IVa) in Scheme 3, can be resolved by converting the mixture of enantiomers into a mixture of diastereoisomers, followed by traditional methods of separation, such as silica chromatography. For example, the racemic alcohol may be allowed to react with a resolving agent, such as a chiral nonracemic compound thereby resulting in the formation of a diastereoisomeric mixture. Preferably, the chiral nonracemic compound is either an acid chloride or a chloroformate, thereby resulting in the formation of a diastereoisomeric mixture of esters or ureas, respectively. The choice of the chiral nonracemic resolving agent will depend on factors known to those skilled in the art. For example, see E. L. Eliel, L. N. Mander *Stereochemistry of Organic Compounds* 1994, Wiley and Sons, p. 322, herein incorporated by reference as related to resolution of racemic mixtures.

An alternative method for resolution includes reacting the racemic mixture of alcohol (formula (IV)) with a lipase enzyme capable of converting one enantiomer of the alcohol into an ester. The ester and the remaining alcohol can then be separated by methods known to those skilled in the art. For more detail, see Eliel, p. 413, herein incorporated by reference as related to resolution of racemic mixtures.

A further method for resolution includes converting the racemic mixture of alcohol (IV) to an appropriate ester derivative (for example, acetate) that subsequently may be resolved into two enantioenriched mixtures by use of an esterase enzyme. Although any appropriate esterification reaction may be used, preferably the alcohol is reacted with an acid chloride or acid anhydride in the presence of an agent capable of acting as a base to provide the desired ester derivative. These reactions may be performed in an aprotic solvent (for example, tetrahydrofuran) and in the presence of a compound capable of acting as a base (for example, sodium carbonate). In addition, a compound capable of acting as a catalyst (for example, 4-N,N-dimethylaminopyridine) preferably may be used.

The resulting racemic mixture of esters may then be allowed to react with an appropriate esterase enzyme under conditions which allow for reaction of predominantly one racemate of the ester, providing a mixture of an enantioenriched alcohol of one stereochemical configuration and enantioenriched ester of the opposite stereochemical configuration. The mixture of alcohol and ester may then be separated using methods known to those skilled in the art, for example silica gel chromatography. The choice of an appropriate esterase enzyme, as well as appropriate reaction conditions, will depend on a number of factors known to those skilled in the art. See, for example, Eliel, p. 409, herein incorporated by reference as related to esterase enzyme reactions. For example,

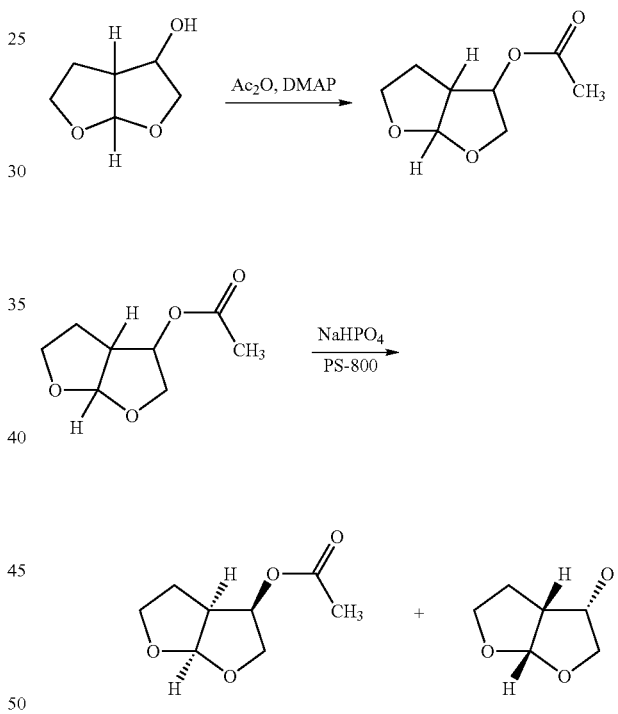

Scheme 4 racemic (3α,3aβ,6aβ)-hexahydrofuro[2,3-b]furan-3-ol was allowed to react with acetic anhydride in a mixture of tetrahydrofuran and methylene chloride, and in the presence of sodium carbonate and 4-N,N-dimethylaminopyridine to yield hexahydrofuro[2,3-b]furan-3-yl acetate. The resulting acetate was then allowed to react with PS-800 in a buffered mixture of sodium hydrogen phosphate while the pH is kept between about 6.2 and 7.2 with the addition of 15% aqueous sodium hydroxide as needed to yield a mixture of (3R,3aS,6aR)-hexahydrofuro[2,3-b]furan-3-yl acetate and (3S,3aR,6aS)-hexahydrofuro[2,3-b]furan-3-ol.

The following examples are for the purpose of illustration only and are not to be construed as limiting the scope of the present invention.

EXAMPLE 1

(3α,3aβ,6aβ)-hexahydrofuro[2,3-b]furan-3-ol

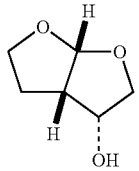
(1)

Step A: 2,7-dioxabicyclo[3.2.0]hept-3-en-6-ylmethoxy](trimethyl)silane

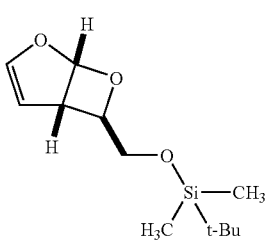
(2)

A flow cell was assembled, consisting of a circulation pump, polytetrafluoroethylene (PTFE) tubing, a 1 L quartz jacketed round-bottom flask, a quartz immersion well, and 4 15 W UVB lamps. Into the flow cell were placed commercially available tert-butyldimethylsilyloxyacetaldehyde (19.44 g, 0.112 mol) and freshly distilled furan (550 mL). The resulting mixture was cooled, stirred under nitrogen, and circulated through the quartz cell using a metered pump. After 48 h, the mixture was transferred to a round bottom flask and the reaction apparatus was washed with dichloromethane and the washings were added to the reaction mixture. The mixture was then condensed under vacuum to afford compound (2) as a yellow oil (28.07 g crude, 104%) that was diluted with tetrahydrofuran (THF) and stored cold. The solution was concentrated under vacuum to afford a yellow oil. Addition of hexanes (1 L) caused a precipitate to form. Activated charcoal (3 g) and Celite (3 g) were added to the mixture, stirred for 20 min, then filtered over a PTFE frit (0.45 □m), the solid was rinsed with hexanes (100 mL) and the resulting solution was concentrated under vacuum to afford compound (2) as a colorless oil (26.5 g, 98%).

$^1$H NMR (300 Hz) δ 6.61 (dt, 1H, J=1.0, 3.1 Hz), 6.27 (dt, 1H, J=1.0, 4.2 Hz), 5.32 (dd, 1H, J=3.0, 3.1 Hz), 4.57 (dt, 1H, J=1.0, 3.1 Hz), 3.81 (dd, 1H, J=3.1, 11.9 Hz), 3.73 (dt, 1H, J=3.1, 11.9 Hz), 3.67 (m, 1H), 0.93 (s, 6H), 0.11 (s, 3H), 0.09 (s, 3H); $^{13}$C NMR (75 MHz, DEPT) 148.0 (3°), 108.0 (3°), 104.0 (3°), 91.5 (3°), 64.8 (2°), 46.0 (3°), 25.9 (1°), −5.32 (1°), −5.46 (1°); IR: 2960, 2924, 2858, 1609, 1470, 1254, 1137, 1049, 982, 837, 782 cm$^{-1}$; HRMS Calcd for $C_{12}H_{23}O_3Si$ (M+1), 243.14158, found 243.14158; LRMS m/z (relative intensity) 243 (M+1), 226 (20), 225 (100), 185 (16), 175 (20), 169 (13), 159 (20), 117 (51), 111 (15), 103 (10), 73 (11).

Step B: 2,7-dioxabicyclo[3.2.0]hept-6-ylmethoxy](trimethyl)silane

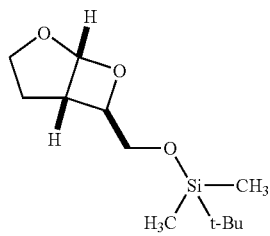
(3)

Into a 1 L Schott flask were placed compound (2) (25.82 g, 0.1065 mol), tetrahydrofuran (THF, 410 mL), 5% w/w platinum on carbon (~50% water) and potassium carbonate (7.85 g). The flask was purged with hydrogen 3 times, finally pressurized to 0.26 barr with hydrogen, and allowed to stir overnight at ambient temperature. The mixture was then purged with nitrogen, Celite (2.9 g) was added, the mixture was filtered through a PTFE membrane (0.45 □m), and the filtrate was washed with THF (100 mL). The resulting solution of compound (3) was used in subsequent reactions without any flirter purification.

Step C:

A THF solution of compound (3) was placed into a flask to which was added water (5 mL) and concentrated hydrochloric acid (3 mL). The resulting mixture was allowed to stir at ambient temperature for 1 h, after which time it was neutralized to pH 7 by the addition of solid sodium carbonate (37 g). The mixture was then filtered and concentrated under vacuum to afford crude (1), which was purified by flash chromatography to afford (1) as a clear oil (1.8 g, 82%). $^1$H NMR was identical to that found in the literature (Ghosh, et. al., *J. Med. Chem.* 1996, 39(17), p. 3278).

EXAMPLE 2

(3R,3aS,6aR)-hexahydrofuro[2,3-b]furan-3-ol

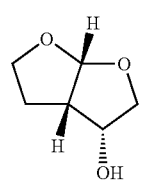
(4)

Step A: (3α,3aβ,6aβ)-hexahydrofuro[2,3-b]furan-3-yl acetate

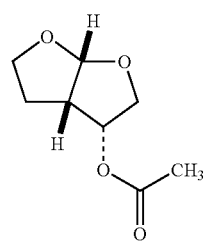
(5)

A reactor was charged with sodium carbonate (2.5 eq., 2.0 wt), compound (1) (above), and 4,4-N,N-dimethylaminopyridine (0.05 eq., 0.04 wt). The resulting mixture was cooled in an ice bath and acetic anhydride (1.5 eq., 1.1 vol) was added at such a rate that the reaction mixture stayed below 10° C. The mixture was then allowed to warm to room temperature and stir overnight. The resulting slurry was filtered through a coarse fritted funnel and the filter cake was washed with methylene chloride (2 vol). The filtrate and washings were combined and were further extracted with 1N HCl (1 vol). The mixture was then concentrated under vacuum to provide hexahydrofuro[2,3-b]furan-3-yl acetate as an oil. $^1$H NMR was identical to that found in the literature (Ghosh, et. al., *J. Med. Chem.* 1996, 39(17), p. 3278).

Alternatively, the intermediate need not be isolated. Namely, to the flask containing the reaction mixture of formula (IV), directly were added compound (1), potassium carbonate, dichloromethane (25 mL), DMAP (0.11 g, 0.09 mmol), and acetic anhydride (15 mL, 0.159 mol) was added in one portion. The resulting mixture was stirred overnight at ambient temperature. An additional portion of acetic anhydride (5 mL, 0.053 mol) was added and the mixture was allowed to stir for 3 h at ambient temperature. Celite was added to the mixture and it was then filtered under vacuum through a pad of Celite, the filtrate was washed with dichloromethane (4×100 mL), and the filtrate was concentrated under vacuum to afford a beige oil. To the oil were added several portions of toluene (3×50 mL) which were removed under vacuum (35 mm Hg, ~50° C.). The oil was then distilled using a Kugelohr apparatus (2 mm Hg, 160° C.) to afford compound (5), above, as a light yellow oil. Analytical data were identical to literature values (Ghosh, et. al., *J. Med. Chem.* 1996, 39(17), p. 3278).

Step B: (3R,3aS,6aR)-hexahydrofuro[2,3-b]furan-3-yl acetate

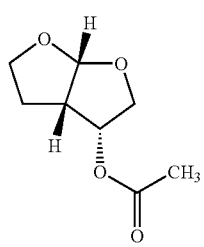

(6)

A reactor was charged with 0.1N NaHPO$_4$ (pH=7.0, 7.5 vol) and (3α,3aβ,6aβ)-hexahydrofuro[2,3-b]furan-3-yl acetate, compound (5), (1 eq., 1 wt). The pH of the solution was then adjusted to 7.0 by the addition of 15% sodium hydroxide and the solution was heated to 35+/−3° C. PS-800 (500 units/mmol) was then added and the pH was kept between 6.8 and 7.2 with the periodic addition of 15% sodium hydroxide. Reaction progress was followed by chiral gas chromatography until all of the undesired acetate had been hydrolyzed. Celite (0.5 wt) was then added, followed by methylene chloride (4.0 vol), and the resulting slurry was stirred for 15 min. The mixture was then filtered through a pad of celite, followed by several washes of the celite pad with methylene chloride. The organic layer was separated and the organic layer was washed with water (3×1 vol), 10% sodium chloride (2 vol) and then was concentrated under vacuum to provide compound (6) as an oil. $^1$H NMR of the title compound was identical to that found in the literature (Ghosh, et. al., *J. Med. Chem.* 1996, 39(17), p. 3278). Typical optical purity of the resulting (3R,3aS,6aR)-hexahydrofuro[2,3-b]furan-3-yl acetate was >98% ee.

Optical purity was determined using chiral GC under the following approximate conditions:
Column: Astec Chiraldex Beta Cyclodextrin Trifluoroacetyl (B-TA) 20 m×0.25 mm;
Carrier gas: He @ 1 mL/min;
Make-up gas: He @ 30 mL/min
Detection: FID @ 300° C.
Injection: 1 uL @ 250° C. (split)
Split flow: 100 mL/min
Total run time: 30 min
Temperature program: Isothermal @ 115° C.
Sample preparation: Approximately 25–50 mg sample (1–2 drops) in 10 mL acetonitrile. Inject 1 uL sample prep. As is known by those of skill in the art, the sample concentration may be adjusted as needed to give adequate sensitivity or to prevent column overloading.
Retention times: (3S,3aR,6aS)-Hexahydrofuro[2,3-b]furan-3-yl acetate=11.43 min;
(3R,3aS,6aR)-Hexahydrofuro[2,3-b]furan-3-yl acetate=12.20 min.

Step C:

A reactor was charged with (3R,3aS,6aR)-hexahydrofuro[2,3-b]furan-3-yl acetate, compound (6), (1 eq., 1 wt), methanol (3 vol) and potassium carbonate (0.001 eq, 0.001 wt). The mixture was allowed to stir at rt for 18–20 h, after which time the reaction mixture was concentrated to afford (3R,3aS,6aR)-hexahydrofuro[2,3-b]furan-3-ol as an oil. $^1$H NMR was identical to that found in the literature (Ghosh, et. al., *J. Med. Chem.* 1996, 39(17), p. 3278). Reaction progress was followed using gas chromatography under the following approximate conditions:
Column: DB-624, 30 m×0.53 mm×3 micron film thickness;
Carrier gas: He at 5 mL/min;
Makeup gas: He at 25 mL/min;
Detector: FID at 300° C.;
Initial oven temperature: 100° C. for 0 min;
Temperature ramp: 20° C./min, to 250° C., followed by a 7.5 min hold.
Retention time of (3R,3aS,6aR)-hexahydrofuro[2,3-b]furan-3-ol=6.55 min.

EXAMPLE 3

(3α,3aβ,6aβ)-hexahydrofuro[2,3-b]furan-3-ol

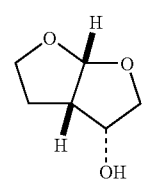

(1)

Step A: (1-methyl-1-phenylethoxy)acetaldehyde

Into a flask were placed commercially available (±)-2,2-dimethyl-1,3-dioxolane-4-methanol (Soketal) (213 mL, 1.7 mol) and xylenes (700 mL). Phenylmagnesium bromide (4 L of a 1.0 M solution in THF) was added in a stream. After the addition was complete, the mixture was heated to 100° C. and the solvent was removed by distillation. The temperature of the mixture was maintained at 100° C. for 42 h, after which it was allowed to cool to 30° C. and a chilled solution of potassium hydrogen phosphate (800 g in 3.6 L of water) was added. The mixture was extracted with ethyl acetate (2×1 L each), the organic layers were combined, filtered through a pad of Celite and concentrated under vacuum. The residue was dissolved in methanol (300 mL), extracted with hexanes (2×200 mL each) and the methanol phase was mixed with silica gel (700 mL) and concentrated under vacuum. The intermediate addition product was purified by flash chromatography on silica gel using a gradient of from 9:1 to 1:9 hexane/ethyl acetate to provide the intermediate addition product (126 g, 36%).

The addition product was added to a flask in addition to dichloromethane (1.4 L) and cooled in an ice bath. To the flask were added silica gel (50 g), water (45 mL) and sodium metaperiodate (180 g). The resulting mixture was warmed to 40° C. during the periodate addition. After 90 min, the mixture was filtered and the residual solids were rinsed with dichloromethane (2×200 mL each). The organic layers were combined and concentrated under vacuum to provide crude aldehyde. The crude aldehyde was purified using a short-path distillation apparatus (2 mm Hg, 83–87° C.) to afford the desired aldehyde (92 g, 78%).

Step B: 6-[(1-methyl-1-phenylethoxy)methyl]-2,7-dioxabicyclo[3.2.0]hept-3-ene

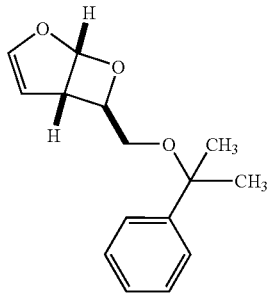

(7)

Compound (7) was prepared as described for the preparation of compound (2), except that (1-methyl-1-phenylethoxy) acetaldehyde was used in place of {[tert-butyl(dimethyl)silyl]oxy}acetaldehyde.

$^1$H NMR (300 MHz) δ 7.5–7.4 (m, 5H), 6.61 (dt, 1H, J=1.0, 2.9 Hz), 6.32 (dt, 1H, J=0.8, 4.2 Hz), 5.33 (t, 1H, J=2.9 Hz), 4.58 (dt, 1H, J=0.8, 3.8 Hz), 3.66 (dddd, 1H, J=0.8, 1.0, 2.9, 4.2 Hz), 3.55 (dd, 1H, J=3.8, 10.7 Hz), 3.42 (dd, 1H, J=3.8, 10.7 Hz), 1.68 (s, 6H); $^{13}$C NMR (75 MHz, DEPT) 147.9 (3°), 145.8 (4°), 128.1 (3°), 126.9 (3°), 125.7 (3°), 108.0 (3°), 104.0 (3°), 90.0 (3°), 76.6 (4°), 64.7 (2°), 46.5 (3°), 28.2 (1°), 28.0 (1°); IR: 2980–2850, 1604, 1504, 1443, 1265, 1160, 1048, 942 cm$^{-1}$; HRMS Calcd for $C_{15}H_{18}O_3Na$ (M+Na), 269.11547, found 269.11548; LRMS m/z (relative intensity) 119 (100), 91 (70), 68 (65).

Step C: 6-[(1-methyl-1-phenylethoxy)methyl]-2,7-dioxabicyclo[3.2.0]heptane

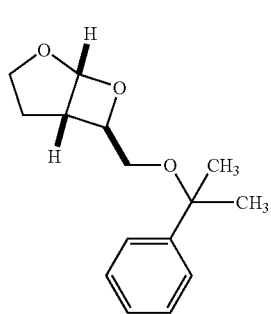

(8)

Compound (7) was reduced to afford compound (8) as described for the preparation of compound (3) from compound (2).

Step D:

Compound (1) was prepared from compound (8) by treatment of (8) with either concentrated hydrochloric acid or with amberlyst catalyst in the same manner as described for the preparation of compound (1) from compound (3).

EXAMPLE 4

(3α,3aβ,6aβ)-hexahydrofuro[2,3-b]furan-3-ol

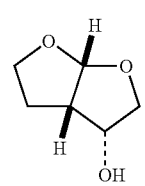

(1)

Step A: 6-(tert-butoxymethyl)-2,7-dioxabicyclo[3.2.0]hept-3-ene

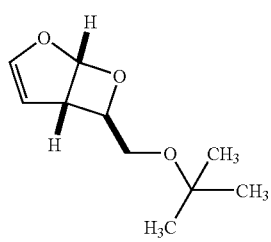

(9)

Compound (9) was prepared using the method for the preparation of compound (2), except that tert-butoxyacetaldehyde (prepared according to the method of M. J. Brown, L. E. Overman, J. Org. Chem. 1991, Vol. 56. P. 1933), was used in place of {[tert-butyl(dimethyl)silyl]oxy}acetaldehyde.

$^1$H NMR (300 MHz) δ 6.61 (dt, 1H, J=1.2, 2.9 Hz), 6.28 (dt, 1H, J=1.0, 4.6 Hz), 5.33 (t, 1H, J=2.9 Hz), 4.60 (dt, 1H, J=1.0, 3.5 Hz), 3.63 (dddd, 1H, J=1.0, 1.2, 2.9, 4.6 Hz), 3.59 (dt, 1H, J=3.5, 10.6 Hz), 3.52 (dd, 1H, J=3.5, 10.6 Hz), 1.22 (s, 9H); $^{13}$C NMR (75 MHz, DEPT) 147.9 (3°), 108.0 (3°), 104.1 (3°), 90.3 (3°), 73.0 (4°), 63.7 (2°), 46.5 (3°), 27.4

(1°); IR: 2980, 2930, 1609, 1470 (br), 1370, 1199, 976, 948 cm$^{-1}$; HRMS Calcd for $C_{10}H_{17}O_3Na$ (M+1), 185.11764, found 185.11764; LRMS m/z (relative intensity) 185 (M+1), 167 (100), 149 (14), 145 (9), 129 (19), 117 (17), 111 (9).

Step B: 6-(tert-butoxymethyl)-2,7-dioxabicyclo[3.2.0]heptane

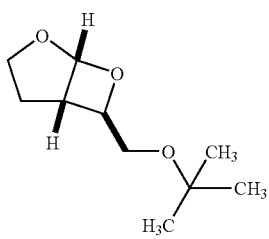
(10)

Compound (9) was reduced to afford compound (10) as described for the preparation of compound (3) from compound (2).

Compound (1) was prepared from compound (10) by treatment of (10) with trifluoroacetic acid in 2,2,2-trifluoroethanol in the same manner as described for the preparation of compound (1) from compound (3).

EXAMPLE 5

6-[(benzyloxy)methyl]-2,7-dioxabicyclo[3.2.0]hept-3-ene

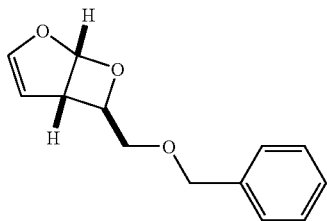
(11)

Compound (11) was prepared using the method for the preparation of compound (2), except that commercially available (benzyloxy)acetaldehyde was used in place of {[tert-butyl(dimethyl)silyl]oxy} acetaldehyde.

$^1$H NMR (300 MHz) δ 7.40–7.10 (m, 5H), 6.65 (m, 1H), 6.35 (dd, 1H, J=0.7, 4.2 Hz), 5.33 (dd, 1H, J=2.8, 2.8 Hz), 4.69 (d, 1H, J=12.1 Hz), 4.66 (m, 1H), 4.60 (d, 1H, J=12.1 Hz), 3.69 (m, 1H), 3.72 (d, 1H, J=0.7 Hz), 3.71 (d, 1H, J=0.7 Hz); $^{13}$C NMR (75 MHz, DEPT) 148.0 (3°), 138.0 (4°), 128.3 (3°), 127.6 (3°), 127.5 (3°), 108.0 (3°), 104.0 (3°), 90.0 (3°), 73.5 (2°), 71.8 (2°0, 46.5 (3°); IR: 3091, 2975, 2941, 2847, 1736, 1609, 1465, 1137, 1048 cm$^{-1}$; HRMS Calcd for $C_{13}H_{14}O_3Na$ (M+Na), 241.08418, found 241.08418.

Although subsequent reduction, deprotection, and rearrangement were not performed for compound (11), the present inventors expect compound (11) to undergo reduction of the olefinic bond as detailed for compound (3) from compound (2), followed by reduction, deprotection, and rearrangement as described for the preparation of compound (1) from compound (3).

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A method for the preparation of a cyclic alcohol of formula (IV)

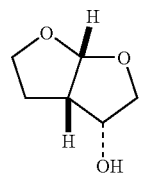
(IV)

comprising reducing, deprotecting, and rearranging, in non-aqueous telescoping conditions, an oxetane of formula (II)

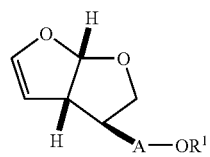
(II)

wherein A is —CH$_2$— and
R$^1$ is
—C(R$^2$)$_3$, where each R$^2$ is independently selected from the group consisting of H, alkyl, and aryl;
—C(O)R$^3$, wherein R$^3$ is selected from the group consisting of alkyl and aryl; or
—Si(R$^3$)$_3$, wherein each R$^3$ is independently as defined above.

2. The method of claim 1 wherein R$^1$ is —C(R$^2$)$_3$, one R$^2$ is —CH$_3$, one R$^2$ is —CH$_3$, and one R$^2$ is phenyl and the reduction, deprotection, and rearrangement is conducted in situ with palladium on carbon with one of formic acid, ammonium formate, or hydrogen.

3. The method of claim 2 wherein the in situ reaction agent is palladium on carbon with hydrogen.

4. The method of claim 3 wherein the catalyst is 10% Pd/C.

5. The method of claim 2 wherein the the reduction, deprotection, and rearrangement is conducted in situ with a solvent selected from the group consisting of methanol, ethanol, ethyl acetate, dimethoxyethane, and THF.

6. The method of claim 5 wherein the solvent is THF.

7. The method of claim 1 wherein R$^1$ is —Si(R$^3$)$_3$, wherein each R$^3$ is C$_{1-8}$ alkyl.

8. The method of claim 1 further comprising:
resolving the cyclic alcohol to provide an enantioenriched mixture.

9. The method of claim 1 further comprising:
resolving the cyclic alcohol to provide an enantiomerically pure cyclic alcohol.

10. A method for the preparation of hexahydrofuro[2,3-b]furan-3-ol, comprising:

a) reacting a compound of formula (I) with furan in the presence of light;

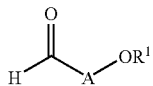

wherein A is —CH$_2$— or —C(O)—, provided that when A is —CH$_2$—

R$^1$ is selected from:
—C(R$^2$)$_3$, where each R$^2$ is independently selected from the group consisting of H, alkyl, and aryl;
—C(O)R$^3$, wherein R$^3$ is selected from the group consisting of alkyl and aryl; or
—Si(R$^3$)$_3$, wherein each R$^3$ is independently as defined above; and when A is —C(O)—,
R$^1$ is selected from alkyl or aryl;
to produce a 2,7-dioxabicyclo[3.2.0]hept-3-ene derivative; and reducing, deprotecting, and rearranging in non-aqueous telescoping conditions the 2,7-dioxabicyclo[3.2.0]hept-3-ene derivative to produce hexahydrofuro[2,3-b]furan-3-ol.

11. The method of claim 10 further comprising:
resolving the hexahydrofuro[2,3-b]furan-3-ol.

12. The method according to claim 11, wherein said resolution further comprises:
i) reacting (3α,3aβ,6aβ)-hexahydrofuro[2,3-b]furan-3-ol with an acylating agent to afford an acyl derivative; and
ii) reacting said acyl derivative with an esterase enzyme to afford (3R,3aS,6aR)-hexahydrofuro[2,3-b]furan-3-ol.

13. The method according to claim 10, wherein when R$^1$ is —Si(R$^3$)$_3$, the method further comprises:
cleaving the silyl group.

14. The method of claim 10 wherein when R$^1$ is —C(O)R$^3$—, the method further comprises a hydride reduction.

15. The method of claim 14 wherein said hydride reduction comprises using an agent selected from the group consisting of aluminum hydride, di-isobutylaluminum hydride, lithium aluminum hydride, borane, and modified sodium borohydride.

\* \* \* \* \*